(12) United States Patent
Cohen et al.

(10) Patent No.: US 7,252,856 B2
(45) Date of Patent: Aug. 7, 2007

(54) BLOOD GAS SYRINGE HAVING IMPROVED BLOOD BARRIER

(75) Inventors: Richmond R. Cohen, Williamsport, PA (US); Preston Keusch, Hazlet, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 597 days.

(21) Appl. No.: 10/625,156

(22) Filed: Jul. 23, 2003

(65) Prior Publication Data

US 2004/0131794 A1 Jul. 8, 2004

Related U.S. Application Data

(62) Division of application No. 09/942,401, filed on Aug. 30, 2001, now Pat. No. 6,648,836.

(51) Int. Cl.
  *B05D 7/22* (2006.01)
  *B05D 3/06* (2006.01)
  *A61B 5/00* (2006.01)
  *B65D 81/00* (2006.01)

(52) U.S. Cl. .................. 427/230; 427/2.3; 427/551

(58) Field of Classification Search ........... 427/2.3, 427/496, 551, 595, 230, 244; 210/506; 261/5
See application file for complete search history.

(56) References Cited

U.S. PATENT DOCUMENTS

| 4,424,817 A | | 1/1984 | Williams ................. 128/766 |
| 4,617,941 A | | 10/1986 | Ichikawa et al. .......... 128/765 |
| 4,743,258 A | * | 5/1988 | Ikada et al. ............. 623/1.49 |
| 4,774,963 A | * | 10/1988 | Ichikawa et al. ......... 600/576 |
| 4,821,738 A | | 4/1989 | Iwasaki et al. ........... 128/765 |
| 5,125,415 A | * | 6/1992 | Bell ........................ 600/579 |
| 5,283,003 A | | 2/1994 | Chen ....................... 252/350 |

FOREIGN PATENT DOCUMENTS

| EP | 0086456 | 2/1983 |
| EP | 1199104 A2 | 10/2001 |
| EP | 1287784 A1 | 8/2002 |
| WO | WO96/17883 | 6/1996 |
| WO | WO01/12746 A1 | 8/1999 |

* cited by examiner

*Primary Examiner*—William Phillip Fletcher, III
(74) *Attorney, Agent, or Firm*—Mark Lindsey

(57) ABSTRACT

A process for fabricating a water-swellable porous plastic plug is provided, the process including the steps of: providing a porous substrate having a plurality of passageways therethrough, disposing into the passageways a hydrophilic polymer, irradiating the substrate to induce cross-linking of the hydrophilic polymer, such that the polymer forms a hydrogel coating on the walls of the passageways.

5 Claims, 2 Drawing Sheets

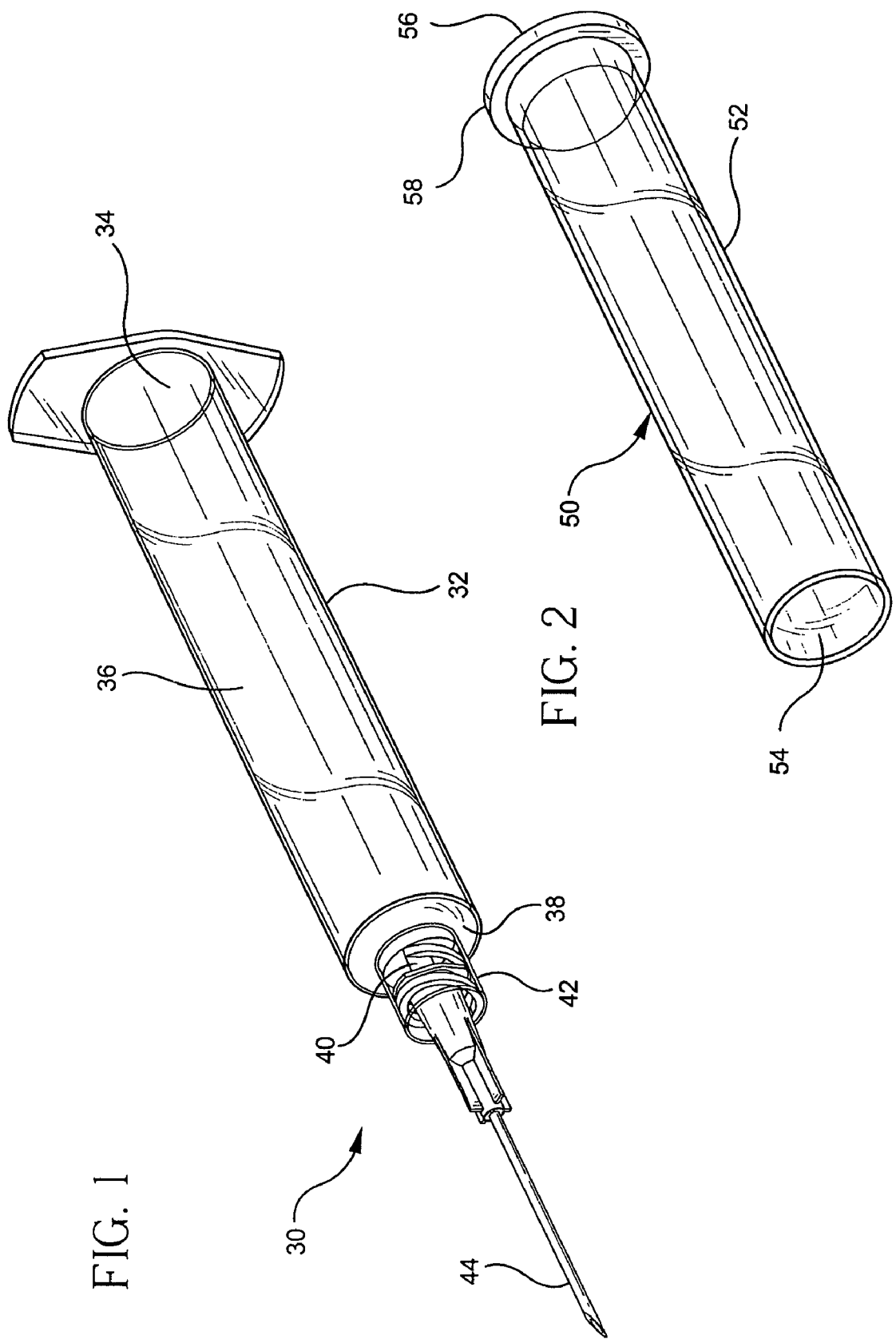

BLOOD GAS SYRINGE HAVING IMPROVED BLOOD BARRIER

The present patent application is a divisional application of Ser. No. 09/942,401 prior U.S. Pat. No. 6,648,836 filed Aug. 30, 2001, the disclosure of which is hereby incorporated by reference.

FIELD OF THE INVENTION

This invention relates to blood sampling, and more particularly relates to a syringe for collecting a blood gas sample having improved air-sample separation means.

BACKGROUND

Samples for blood gas analysis have conventionally been collected in syringes having some means to vent air in the syringe prior to sample collection and to protect the sample from external air after collection. Many prior art devices accomplish venting with a filter across a hollow plunger rod which allows passage of air, but not blood, from the interior of the syringe during collection. U.S. Pat. No. 4,821,738 uses a hydrophobic filter and is exemplary of this art. U.S. Pat. No. 4,424,817 uses filters of paper or styrofoam and, in one embodiment, uses two filters, one hydrophilic and one hydrophobic.

U.S. Pat. No. 5,238,003 includes a perforated or slotted disc having upper and lower faces which enclose a hydrophobic filter. The patent adds additional structure which allows the syringe plunger to be advanced during sample collection and thereby overcomes the problem, imposed by conventional fixed plungers, which may cause insufficient sample collection from a patient having low blood pressure.

SUMMARY OF THE INVENTION

A porous substrate includes a plastic body portion having a hydrogel coated thereon. In this disclosure the term hydrogel is used to designate a crosslinked polymeric coating on the substrate surface, and the term hydrophilic polymer is used to designate the material which upon crosslinking gives the hydrogel.

The porous substrate may be a component of a medical article. The preferred article is an arterial blood gas syringe having a barrel and a hollow plunger rod wherein the substrate is a plug fitted into the rod. The preferred hydrophilic polymer is polyvinyl pyrrolidone (PVP) and the preferred hydrogel is PVP which has been crosslinked and bound to an inside wall surface of a pore of the plug by electron beam or gamma irradiation.

The plug is permeable to air until the hydrogel coating swells by absorption of water when in contact with blood. The swelling closes the pores to passage of both air and blood and thereby seals the blood sample from the external environment. Because the hydrogel is permanently affixed to the article surface, it cannot be washed away by contact with the blood. The coating is applied without use of any environmentally unfriendly solvents, and the article may be sterilized by radiation used to crosslink the polymer and bind the resulting hydrogel to the substrate.

BRIEF DESCRIPTION OF THE DRAWINGS

FIG. 1 is a perspective view of a syringe barrel of the invention;

FIG. 2 is a perspective view of a conventional syringe plunger rod for use with the barrel of FIG. 1;

DETAILED DESCRIPTION

Figure 4:
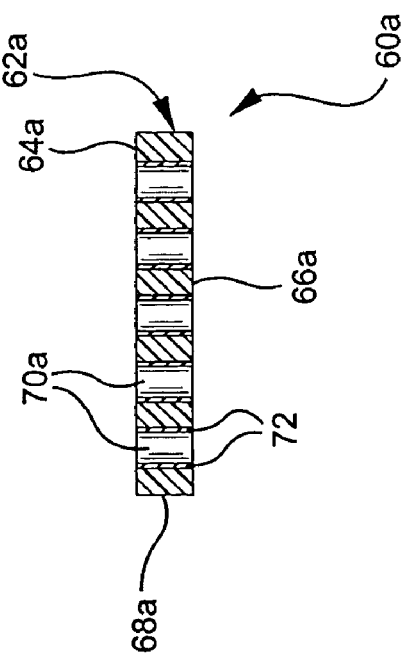
FIG. 4 is a vertical sectional view of the plug of FIG. 3 taken along the line 4-4a thereof illustrating the hydrophilic coating on the inside wall of the pores.

While this invention is satisfied by embodiments in many different forms, there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

There are many devices designed to collect an aqueous sample and immediately seal the sample from contact with air. In the medical device field, blood gas syringes are representative of such devices. The invention will henceforth be described in detail for a blood gas syringe with the understanding that the invention contemplates any device in which a collected sample of liquid must be sealed from contact with the surrounding atmosphere.

Adverting now to the drawings, FIG. 1 illustrates a conventional syringe barrel 30. Barrel 30 includes a generally tubular member 32 having an open top end 34 and a side wall 36. A bottom wall 38 includes a tube portion 40 affixed to a conventional hub 42 for immobilization of a conventional hypodermic needle 44.

In FIG. 2, syringe plunger 50 has a rod portion 52 and an open proximal end 54. A top wall 56 has an annular projection 58 for advancing and retracting the rod in the barrel when the assembly is in use. Rod 50 is dimensioned to have a sliding and sealing relationship to body portion 32 of barrel 30.

Figure 3:
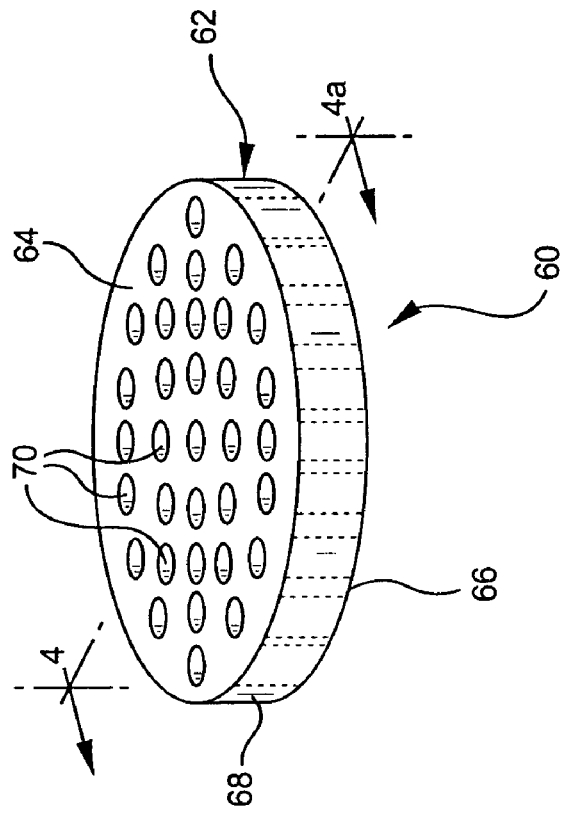
FIG. 3 is a perspective view of the porous plug of the invention.

FIG. 3 illustrates a porous plug 60 adapted for insertion into open proximal end 54 of the plunger rod of FIG. 2. Plug 60 has a plastic body portion 62, a top wall 64, a bottom wall 66, a side wall 68, and pores or passageways 70 therethrough. Plug 60 fits securely within the proximal end 54 of plunger rod 50. The plunger rod-plug assembly fits snugly within barrel 30 so that rod 50 slides sealingly against the barrel inside wall. Although not shown in the drawings, a conventional lubricant, such as polydimethyl siloxane, may be positioned between the barrel and the plunger rod.

FIG. 4 illustrates coating 72 of a hydrogel on the walls of passageways 70a.

When the rod-plug assembly is positioned within barrel 30, an interior volume is formed bounded by plug 60 in open end 54 of the rod, side wall 36 and bottom wall 38 of the barrel.

The plastic body portion of the plug of the invention may be a solid block of polymer having pores or passageways therethrough. Alternatively, the body portion may be in the form of a foam. Suitable polymers for the body portion of the plug are polyolefins such as polyethylene (PE), polytetrafluoroethylene and polypropylene, polyesters such as polyethylene terephthalate, polystyrene, polyurethane, polyvinylchloride, polyacrylic and mixtures or copolymers thereof. The preferred substrate material is PE.

The hydrophilic polymer may be a polyalkyleneoxide, such as polyethyleneoxide (PEO) and polypropylene oxide, PVP, polyvinyl alcohol, polyvinylacetate (PVA), polyhydroxyalkyl acrylates, polystyrene sulfonate and mixtures or copolymers thereof, such as PVP-PVA. Choice of suitable polymers for hydrogel formation is well within the purview of one skilled in the polymer arts, and no further details regarding this aspect of the invention are needed for a full understanding by one skilled in the art.

For the most preferred hydrophilic polymer, PVP, the molecular weight may be 25,000 to 2,500,000, preferably 60,000 to 2,500,000, most preferably 600,000 to 1,500,000.

To prepare the plug, the PVP may be dissolved in water at a concentration of about 2-30, preferably 20-30% by weight. This solution may then be applied to a surface of the body portion of plug by any conventional method such as dipping or spraying. In order to assure that the walls of the passageways of the plug are coated, the solution is preferably applied under pressure or by prior evacuation of the passageways.

The coating of PVP may then be partially, but not completely, dried by any convenient procedure which leaves enough residual water to enable hydrogel formation. The quantity of water remaining is not critical, and may conveniently be about 1-20, preferably about 2-10% by weight of the polymer.

The hydrophilic polymer may then be crosslinked to the hydrogel and bound tightly to the substrate by gamma or electron beam irradiation at a dose (0.3 to 5.0 Mrad, 3 kgy to 50 kgy), preferably about 1 Mrad (10 kgy) to effect sterilization of the plug. After irradiation, the plug is preferably dried in an oven or under ambient conditions. In this way, the hydrogel is not swollen and the passageways are permeable to gas. Advantageously, the hydrogel in this state is not water soluble, does not absorb moisture vapor, does not swell during storage, and is permanently affixed to the plug body portion.

To take a blood sample with the blood gas syringe of the invention, the plunger of FIG. 2 having the plug of FIGS. 3 and 4 in open end 54 is advanced in the barrel until bottom wall 66 of the plug meets bottom wall 38 of the barrel of FIG. 1. Needle 44 is then inserted into the patient's artery, and plunger rod 50 is retracted causing blood to flow into the barrel. Any air present in the system is forced out through the hydrogel-coated passageways of the plug by the advancing blood. Blood continues to enter the interior volume bounded by the plug and side and bottom walls of the barrel under the arterial pressure, forcing any air out through the plug, until the blood contacts the plug in the plunger rod. The hydrogel immediately absorbs water from the blood, swells and seals the passageways, effectively halting all blood flow. It is easily seen that the size of the sample taken depends on how far the plunger is retracted.

Alternatively, the rod-plug assembly is preset at a given interior volume in accordance with the size of the sample desired.

EXAMPLE 1

A 24% aqueous solution (by weight) was prepared by mixing 240 g of PVP K90, obtained from ISP, Wayne, N.J., with 760 g of deionized water at 20° C. After complete dissolution of the PVP, the solution was degassed on standing, and the solution then placed into a petri dish. Untreated polyethylene porous plugs were obtained from Porex Technologies, Inc., Fairburn, Ga., and the plugs were immersed in the PVP solution for two minutes. Excess solution was allowed to drain from each plug, and the plugs were then attached to the end of syringe plungers from Vacutainer™ Brand Critical Care Blood Collection System, 3-mL Preset™ Syringes (Becton Dickinson and Co.) The plugs were partially dried for approximately six hours at ambient conditions. The plugs were still wet when they were subjected to gamma irradiation at a dosage of about 4.2-4.8 Mrad. Following irradiation, the plugs were dried at 70° C. overnight to remove all moisture.

The plug-plunger rods were then manually assembled into complete prototype 3-mL syringes. To test for venting, a syringe was pulled halfway back, and the luer-lock end of the syringe was secured to an airtight fitting piece (KippMed T-adapter made by Kipp Group, Ontario, Calif., USA) attached to an air supply. The third side of the adapter was sealed off with adhesive (Loctite 4061). Also, a pressure gauge was hooked into the tubing carrying the air. Opening a valve activated the flow of air. The valve was adjusted until the pressure on the gauge read about 2 psi. The syringe and T-adapter-assembly were then immersed in a water bath. The air flowed into the tip of the syringe, through the treated porous plug, and out the distal end of the syringe, producing visible bubbling in the bath. The rate of bubbling was similar to that of the control syringe (Vacutainer™ Brand Critical Care Blood Collection System, 3-mL Preset™). This demonstrated that the prototype plugs were still permeable to gas after treatment.

Then, about 1.6 mL of deionized water was drawn into a prototype syringe through the tip, contacting the top surface of the treated porous plug. The prototype syringe was once again submerged in the water bath. This time, there was no bubbling (as well as for the control syringes) in the bath. This demonstrated that the exposure of the plug to the water swelled the PVP hydrogel and rendered the plugs impermeable to gas.

EXAMPLE 2

Porous plugs were coated with a 30% solution of K90 PVP in water by immersion for one hour. Excess solution was drained and the plugs were partially dried for approximately six hours at ambient conditions. The plugs, still wet, were assembled to the plungers of Vacutainer™ Brand Critical Care Blood Collection System, 3 mL Preset™ syringes and were then subjected to gamma irradiation at a dosage of about 1.4-1.8 Mrad. Following irradiation, the plugs were dried at 70° C. overnight to remove all moisture.

Plugs were then manually assembled into complete prototype 3 mL syringes. A syringe and T-adapter-assembly were then immersed in a water bath, as in the previous example. The air flowed into the syringe tip through the treated porous plug and out the distal end of the syringe, producing visible bubbling in the bath. This demonstrated that the plugs were still permeable to gas after treatment.

Then, about 1.6 mL of DI water was drawn into the syringe contacting the top surface of the treated porous plugs. The prototype once again was hooked up to the T-adapter. This time, when the syringe was submerged in the water bath, there was no bubbling in the bath, just as for the control syringes. This demonstrated that the exposure of the plugs to the water was sufficient to swell the PVP hydrogel and render the plugs impermeable to gas.

What is claimed is:

1. A process for fabricating a porous plug, comprising the steps of
   providing a porous substrate comprising a plurality of passageways therethrough,
   disposing into the passageways a hydrophilic polymer,
   subsequent to the disposing step, irradiating the substrate and the hydrophilic polymer, to induce cross-linking of the hydrophilic polymer, such that the polymer forms a hydrogel coating on the walls of the passageways, wherein the hydrogel coating swells upon contact with water.

2. The process of claim 1, wherein the porous substrate is formed from a plastic.

3. The process of claim 1, wherein the hydrophilic polymer is selected from the group consisting of polyalkyleneoxides, polyvinylpyrrolidone, polyvinyl alcohol, polyvinylacetate, polyhydroxyalkyl, polystyrene sulfonate, and mixtures thereof.

4. The process of claim 3, wherein the hydrophilic polymer is polyvinylpyrrolidone.

5. The process of claim 1, wherein the irradiation is gamma irradiation or electron beam irradiation.

* * * * *